United States Patent
Tiers

(10) Patent No.: US 6,350,925 B1
(45) Date of Patent: Feb. 26, 2002

(54) PERHALOETHYL AROMATIC COMPOUNDS AND PERHALOETHENYL AROMATIC COMPOUNDS THEREFROM

(75) Inventor: George Van Dyke Tiers, Saint Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/126,784

(22) Filed: Jul. 31, 1998

(51) Int. Cl.$^7$ .......................... C07C 17/00; C07C 22/08
(52) U.S. Cl. ................. 570/125; 570/126; 570/127; 570/128; 570/129; 570/138; 570/144
(58) Field of Search .................. 521/27, 32, 33, 521/31; 526/242, 243, 247, 248, 249, 278, 286, 287, 291, 292.8, 292.9, 826; 570/125, 126, 127, 128, 129, 138, 144

(56) References Cited

U.S. PATENT DOCUMENTS

| | | |
|---|---|---|
| 3,002,030 A | 9/1961 | Hauptschein et al. |
| 3,006,973 A | 10/1961 | Hauptschein et al. |
| 3,271,441 A | 9/1966 | Brace |
| 3,281,426 A | 10/1966 | Tiers |
| 3,449,449 A | 6/1969 | Nichols et al. |
| 3,489,807 A | 1/1970 | Shingu et al. |
| 4,012,303 A | 3/1977 | D'Agostino et al. |
| 4,107,005 A | 8/1978 | D'Agostino et al. |
| 4,113,922 A | 9/1978 | D'Agostino et al. |
| 5,422,411 A | 6/1995 | Wei et al. |
| 5,498,639 A | 3/1996 | Wei et al. |
| 5,602,185 A | 2/1997 | Stone et al. |
| 5,684,192 A | 11/1997 | Stone et al. |
| 5,773,480 A | 6/1998 | Stone et al. |

OTHER PUBLICATIONS

Database CAPLUS on STN, Acc. No. 1972:551653, Bollinger et al., 'Benzylamines.' DE 2104313 abstract.*
Database CAPLUS on STN, Acc. No. 1972:140154, Brovko et al., 'Beta–chloronanafluoroethylbenzene and perfluoro–1, 2–diphenylethane.' SU 328081 (abstract), 1972.*
Database CAPLUS on STN, Acc. No. 1977:534764, Karpov et al., 'Themolytic reactions of polyfluoroorganic compounds XVIII. Copyrolysis of pentafluorophenol with trifluorochlorethylene.' Novosib. Inst. Org. Khim., Novosibirsk, USSR Izv. Sib. Otd. Akad. Nauk SSSR, Ser. Khim. Nauk (1977), (2), pp. 129–133 (Abstract).*
Chemical Abstracts, vol. 54, (1960), p. 4159e.*
Database CAPLUS on STN, Acc. No. 87:67925, Rondestvedt, 'Meerwein arylation of fluorinated olefins.' J. Org. Chem. (1977), 42(15), p. 2618–20. (abstract).*
Database CAPLUS on STN, Acc. No. 1968:69658, Hodgdon, 'Polyelectrolytes prepared from perfluoroalkylaryl macromolecules.' J. Polym. Sci., Polym. Chem. Ed. (1968), 6(1), pp. 171–191 (abstract).*
Database CAPLUS on STN, Acc. No. 1995:17491, Yamomoto et al.. 'The preparation and thermal dimerization study ofa trifluorovinyl–containing imide. Application to the synthesis of a trifluorovinyl–containing polyimide precursor.' Macromol. Symp. (1994), 8.*
Hodgdon, Polyelecrolytes Prepared from Perfluoroalkylaryl Macromolecules, J. Polymer Sci., 6:171–191 (1968) ("Hodgdon").
Cohen et al., α, β, β–Trifluorostyrene and α–Chloro–β, β–Difluorostyrene, J.Am.Chem.Soc., 71(10):3439–3440 (1949) ("Cohen").
Tiers, Perfluoroalkylation of Aromatic Compounds, J.Am.Chem.Soc. 82:5513 (1960); U.S. Pat. No. 3,281,426; U.S. Pat. No. 3,271, 441; Kamigata et al, Direct Perfluoroalkylation of Aromatic and Heteroaromatic Compounds, J. Chem Soc. Perkin Trans. 1:1339–1346 (1994).
Knunyants and Shokina, ω–Phenylperfluoro–α–Olefins and ω–Phenylperfluoroalkanoic Acids, J.Acad.Sci.SSSR, Chem.Ser., pp. 68–71 (Jan., 1967).

* cited by examiner

Primary Examiner—Brian J. Davis
(74) Attorney, Agent, or Firm—Philip Y Dahl

(57) ABSTRACT

A synthesis is provided for α,β-difluoro-β-halo-ethenyl aromatic compounds such as α,β,β-trifluorostyrenes by a process of reacting $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3, and subsequently dechlorohalogenating this product to form $(CFX=CF)_n$—Ar. Novel synthetic intermediate compounds are provided.

21 Claims, No Drawings

PERHALOETHYL AROMATIC COMPOUNDS AND PERHALOETHENYL AROMATIC COMPOUNDS THEREFROM

FIELD OF THE INVENTION

This invention relates to a process that comprises reacting $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3. This product may then be dechlorohalogenated to form $(CFX=CF)_n$—Ar.

BACKGROUND OF THE INVENTION

Polymers of various α,β,β-trifluorostyrenes are used to fabricate ion-exchange membranes and solid polymer electrolytes for use in electrochemical applications such as fuel cells. Polymers containing monomer units based on α,β,β-trifluorostyrene sulfonic acid (I) are typically used. Polymers containing monomer units based on other α,β,β-trifluorostyrene derivatives are also used. See U.S. Pat. Nos. 4,012,303, 4,107,005 (division) and 4,113,922 (division); and U.S. Pat. No. 5,422,411, 5,498,639 (continuation), U.S. Pat. No. 5,602,185 (CIP), U.S. Pat. No. 5,684,192 (division of CIP) and U.S. Pat. No. 5,773,480 (CIP).

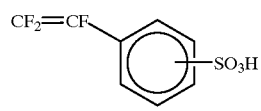
(I)

Hodgdon, *Polyelectrolytes Prepared from Perfluoroalkylaryl Macromolecules*, J. Polymer Sci., 6:171–191 (1968) ("Hodgdon") discloses a many-step synthesis of α,β,β-trifluorostyrene starting from trifluoroacetophenone and Grignard reagent phenyl magnesium bromide, followed by polymerization of the monomer and partial sulfonation of the resulting poly-α,β,β-trifluorostyrene. U.S. Pat. Nos. 5,602,185 and 5,684,192 (division) disclose a many-step synthesis of p-sulfonyl fluoride-α,β,β-trifluorostyrene via p-iodobenzenesulfonylfluoride. U.S. Pat. No. 3,449,449 discloses a synthesis of α,β,β-trifluorostyrene from phenyl sodium and tetrafluoroethylene. U.S. Pat. No. 3,489,807 discloses pyrolytic reaction of phenyl chlorofluoromethane and chlorodifluoromethane at very high temperature which results in mixtures of perfluoroethylene, α,β,β-trifluorostyrene and difluorostilbene. Cohen et al., *α,β,β-Trifluorostyrene and α-Chloro-β,β-Difluorostyrene*, J.Am.Chem.Soc., 71(10):3439–3440 (1949) ("Cohen") discloses a synthesis of α,β,β-trifluorostyrene which begins with a Friedel-Crafts reaction of trifluoroacetyl chloride with benzene in the presence of aluminum chloride.

Addition of perfluoroalkyl groups to aromatic compounds has been demonstrated. Tiers, *Perfluoroalkylation of Aromatic Compounds*, J.Am.Chem.Soc. 82:5513 (1960); U.S. Pat. No. 3,281,426; U.S. Pat. No. 3,271,441; Kamigata et al, *Direct Perfluoroalkylation of Aromatic and Heteroaromatic Compounds*, J. Chem Soc. Perkin Trans. 1:1339–1346 (1994). Addition of C4 or larger dichloroperfluoroalkyl groups to aromatic compounds and subsequent dechlorination to olefins has been demonstrated. Knunyants and Shokina, *ω-Phenylperfluoro-α-Olefins and ω-Phenylperfluoroalkanoic Acids*, J.Acad.Sci.SSSR, Chem.Ser., pp. 68–71 (January, 1967).

SUMMARY OF THE INVENTION

Briefly, the present invention provides a process of reacting $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3. This product may then be dechlorohalogenated to form $(CFX=CF)_n$—Ar. The resulting α,β,β-difluoro-β-halo-ethenyl aromatic compounds, which are preferably α,β,β-trifluoroethenyl aromatic compounds, may be polymerized or copolymerized and may be derivatized, e.g. by sulfonation, before dechlorohalogenation or after polymerization.

In another aspect, the present invention provides a reaction intermediate $(CFCl_2CF_2)_n$—Ar, wherein X is F or Cl, n is 1, 2 or 3 and Ar is unsubstituted benzene.

In another aspect, the present invention provides a reaction intermediate $(CFX_2CFX)_n$—Ar, wherein each X is independently F or Cl, provided that at least one X of each $(CFX_2CFX)$ group is Cl and at least one X of each $(CFX_2CFX)$ group is F, wherein n is 1, 2 or 3 and wherein Ar is selected from the group consisting of monosubstituted benzene, disubstituted benzene and polysubstituted benzene bearing three or more substituents.

What has not been described in the art, and is provided by the present invention, is a relatively simple, inexpensive and effective synthetic route to α,β-difluoro-β-halo-ethenyl aromatic compounds such as α,β,β-trifluorostyrene and derivatives thereof. Furthermore, such a synthetic route involving addition to an aromatic compound bearing electronegative substituents has not been described.

In this application "dechlorohalogenation" refers to removal of a chlorine atom and another halogen atom, which may be chlorine or fluorine, from a molecule, e.g., removal of Cl and F from $CF_2ClCF_2$—Ar to form $CF_2=CF$—Ar or removal of Cl and Cl from $CF_2ClCFCl$—Ar to form $CF_2=CF$—Ar;

"substituted" means substituted by conventional substituents which do not interfere with the desired product, e.g., substituents can be alkyl, alkoxy, aryl, phenyl, halo (F, Cl, Br, I), cyano, nitro, etc; and "carbonyl-attached", "sulfonyl-attached" and "phosphonyl-attached" refers to substituents that are attached to the substituted molecule at a carbonyl, sulfonyl or phosphonyl group (respectively) of the substituent.

As used herein, Ar represents an aromatic compound as specified or, where appropriate, a monovalent, divalent or trivalent moiety derived therefrom by removal of one, two or three hydrogens.

It is an advantage of the present invention to provide a relatively simple, inexpensive and low temperature synthetic route to α,β-difluoro-β-halo-ethenyl aromatic compounds, including those bearing electronegative substituents and those used to fabricate ion exchange membranes or solid polymer electrolytes for use in electrochemical applications such as fuel cells.

DETAILED DESCRIPTION OF PREFERRED EMBODIMENTS

The present invention provides a process of reacting $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3. This product may then be dechlorohalogenated to form $(CFX=CF)_n$—Ar. The resulting α,β-difluoro-β-halo-ethenyl aromatic compounds, which are preferably α,β,β-trifluoroethenyl aromatic compounds, may be polymerized or copolymerized and may be derivatized, e.g. by sulfonation, before dechlorhalogenation or after polymerization.

The aromatic starting compound may be any aromatic compound which will react in the present process. Such aromatic compounds must have at least one hydrogen bound to an aromatic carbon. Preferably, the aromatic compound is based on benzene, naphthalene, thiophene, phenanthrene or biphenyl. Most preferably the aromatic compound is based on benzene. The aromatic starting compound may be unsubstituted, monosubstituted, disubstituted or polysubstituted with three or more substituents. Preferred substituents include halogens, such as fluorine, mono- or polyhalogenated alkyl groups, which preferably contain 1–8 carbons and more preferably 1–3 carbons and are preferably perfluoroalkyl groups, aryl groups, halogenated oxa-alkyl groups, aryl ether groups, carbonyl-attached groups, such as fluorocarbonyl and keto aryl groups, sulfonyl-attached groups, such as fluorosulfonyl, aryl sulfones and aryl sulfonate esters, and phosphonyl-attached groups, such as difluorophosphonyl groups. Most-preferred substituents include phenyl, fluoro, perfluoroalkyl, in particular trifluoromethyl, and fluorosulfonyl (—$SO_2F$). The aromatic starting compound may be made by any known process.

The use of aromatic starting compounds that are disubstituted, or polysubstituted with three or more substituents, may lead to syntheses of monomers, polymers and copolymers which were previously difficult or impossible to obtain. These include monomers, polymers and copolymers containing moieties such as 3,5-bis-(fluorosulfonyl)phenyl, 3,5-bis-(trifluoromethyl)phenyl, or 3-trifluoromethyl-5-fluorophenyl.

The iodoperhaloethane reactant is $CFX_2CFXI$, wherein each X is independently F or Cl, provided that at least one X is Cl and at least one X is F. Thus the iodoperhaloethane reactant is selected from $CF_2ClCFClI$, $CF_2ClCF_2I$, $CF_3CFClI$, and $CFCl_2CF_2I$. $CF_2ClCFClI$ and $CF_3CFClI$ have the previously unrecognized advantage that they are more reactive with the aromatic compound as a result of the presence of a chlorine atom on the carbon bearing the iodine atom. The most preferred is $CF_2ClCFClI$, which furthermore results in a product which is more readily dechlorohalogenated. $CF_2ClCF_2I$ has the advantage that it can be made as a single isomer by addition of ICl to $C_2F_4$. The use of $CF_2ClCFClI$, $CF_2ClCF_2I$ or $CF_3CFClI$ results in trifluoroethenyl compounds after dechlorohalogenation. However, the use of $CFCl_2CF_2I$ results in chlorodifluoroethenyl compounds after dechlorohalogenation, which do not polymerize as readily as trifluoroethenyl compounds.

The iodoperhaloethane reactant may be made by any suitable method. In one such method, ICl can be added to $C_2ClF_3$ at −10° to 50° C. to form a mixture of $CF_2ClCFClI$ and $CCl_2FCF_2I$. The mixture of isomers may be separated before reaction with the aromatic compound. The mixture may also be used as is in the reaction of the present invention without separation. It has been found that $CF_2ClCFClI$ is more reactive than $CCl_2FCF_2I$. Alternately, ICl can be added to $C_2F_4$ to form $CF_2ClCF_2I$. $CF_2ClCF_2I$ and $CF_3CFClI$ can be made by the method of U.S. Pat. No. 3,006,973 by adding IF to CF=CFCl, wherein IF is generated in situ by the reaction of $I_2$ and $IF_5$.

It has been discovered that the aromatic compound and the iodoperhaloethane reactant will react to replace the iodine atom by the aryl group under the appropriate conditions of heat and pressure, preferably at 290° C. or less, more preferably at 200° C. or less, and even more preferably at 160° C. or less, at the autogenous pressure generated in an autoclave or reaction vessel. Without wishing to be bound by theory, it is understood that the reaction proceeds by way of a free radical intermediate generated by removal of iodine from the iodoperhaloethane reactant. Lower temperatures and pressures may be achieved where additional means of generating free radicals are used. Such free radical generators include UV light and reagents such as tri-iron dodecacarbonyl and peroxides such as t-butyl peroxide.

A means of removing or trapping HI generated during the reaction can be used to advantage. HI generated during the reaction of the aromatic compound with $CF_2XCFXI$ attacks unreacted $CF_2XCFXI$ to form $CF_2XCFXH+I_2$. This effectively wastes half of the iodoperhaloethane reactant. Addition of an acid acceptor such as sodium acetate is one such means to remove or trap HI.

Iodine ($I_2$) may be added to the initial reaction mixture to inhibit dimerization of the iodoperhaloethane reactant.

Preferably the reaction proceeds by addition of one iodoperhaloethane per aromatic compound to form products of the formula $(CFX_2CFX)$—Ar. Since the perhaloethyl substituent is meta-directing, a second and third perhaloethane substituent may be added, resulting in the formation of bis- and tris-iodoperhaloethyl aromatic compounds of the formulae $(CFX_2CFX)_2$—Ar and $(CFX_2CFX)_3$—Ar. These may be recovered from the higher boiling fractions of the reaction mixture. Upon dechlorohalogenation, these compounds will yield $(CF_2=CF)_2$—Ar or $(CF_2=CF)_3$—Ar, which may be used as crosslinking monomers. The higher boiling products may also include heterosubstituted bis- and tris-iodoperhaloethyl aromatic compounds. For example, in the case where the iodoperhaloethane reactant used is a mixture of $CF_2ClCFClI$ and $CCl_2FCF_2I$, these products may include $(CF_2=CF)_q$—Ar—$(CF=CFCl)_r$, where q+r=2 or 3. These products may be useful, for example, to introduce into poly-α,β,β-trifluorostyrene a styrene monomer with pendent unsaturated group, i.e. the less polymerizable (CF=CFCl) group.

The resulting product, $(CFX_2CFX)_n$—Ar, may be dechlorohalogenated (i.e. removal of X, X) to form $(CFX=CF)_n$—Ar. Dechlorohalogenation may proceed by any suitable method, but is most advantageously performed by contacting the product with metallic zinc, preferably in the presence of a beneficial solvent, for example tetrahydrofuran (THF). This well known reaction was first used to prepare α,β,β-trifluorostyrene by Cohen et al. Numerous variants have subsequently been disclosed.

The $(CFX_2CFX)_n$—Ar product may be derivatized by any suitable means prior to dechlorohalogenation. Derivatization includes addition of any suitable substituent, including halogenation, sulfonation, halosulfonation, nitration, etc.

Where the resulting product contains (CF$_2$=CF)— groups, it may be polymerized, including copolymerized, by any appropriate method such as disclosed in U.S. Pat. Nos. 5,602,185 and 5,773,480. The resulting polymer may be derivatized by any suitable means, including addition of any suitable substituent, including halogenation, sulfonation, halosulfonation, nitration, etc.

product was decanted from iodine crystals and, as shown in Table 1, determined to contain about 35 g of a mixture of 23% by weight 1-phenyl-2,2-dichloro-1,1,2-trifluoroethane (the alternate product) and 33% by weight 1-phenyl-1,2-dichloro-1,2,2-trifluoroethane (the preferred product), by NMR spectroscopy (Varian INOVA 400 spectrometer, Varian Associates, Inc., Lexington, Mass.) and gas chromatography using a Hewlett-Packard 5890 chromatograph (Hewlett-Packard Instruments, Palo Alto, Calif.).

TABLE 1

Reactions of 0.50 moles (139.41 g) of C$_2$Cl$_2$F$_3$I[a] with Ar—H

| Ex # | Ar—H | wt., g | Mols | Temp, °C. | Time, Hr | Decanted Product wt.,[b] g | C$_2$Cl$_2$F$_3$Ar weight, g | | | Product Isomer % | |
|---|---|---|---|---|---|---|---|---|---|---|---|
| | | | | | | | By GC | By NMR | By Fract. Dist'n | CClF$_2$CFClAr % (by GC/by NMR) | 3- (or 5-) subst., % |
| 1 | C$_6$H$_6$ | 58.6 | 0.75 | 200 | 17.5 | 108.8 | 36 | 33 | — | 78.3/76.3 | na |
| 2 | C$_6$H$_6$ | 58.6 | 0.75 | 175 | 70 | 136.6 | 37 | 30 | 36.0 | 87.0/86.2 | na |
| 3 | C$_6$H$_5$SO$_2$F | 56.1 | 0.35 | 230 | 21 | 96.3 | 32 | 37 | 34.5[d] | 81.1/80.0 | 87 |
| 4 | C$_6$H$_5$SO$_2$F | 56.1 | 0.35 | 160 | 90 | 191.3 | 3 | 3 | — | 88/— | — |
| 5 | C$_6$H$_5$CF$_3$ | 73.1 | 0.5 | 230 | 40 | 95.6 | 44 | 49 | 55.5[d] | 69/69.8 | 77 |
| 6 | C$_6$H$_5$CF$_3$[c] | 29.2 | 0.20 | 290 | 18 | 66.8 | — | — | 30.0 | — | — |
| 7 | 1,3-C$_6$H$_4$(CF$_3$)$_2$[e,f] | 64.2 | 0.3 | 270 | 50 | 111.2 | 28 | 30 | 23.2[d] | 77/78.3 | 100 |
| 8 | 1,2,4-C$_6$H$_3$F$_3$[e] | 23.2 | 0.175 | 230 | 20 | 189.0 | 8.6 | — | — | 50/— | — |
| 9 | 1,2,4-C$_6$H$_3$F$_3$[e] | 23.2 | 0.175 | 280 | 16 | 96.6 | 16 | — | — | 57/— | — |

— means no data obtained
na means not applicable
[a]Isomer ratio: 62% ClCF$_2$CFClI: 38% Cl$_2$CFCF$_2$I
[b]Approximately 90% recovery of product
[c]0.40 mol C$_2$Cl$_2$F$_3$ used
[d]CH$_2$Cl$_2$ wash included; approximately 100% recovery
[e]C$_2$Cl$_2$F$_3$I isomer ratio: 43% CClF$_2$CFClI: 57% CCl$_2$FCF$_2$I
[f]0.70 mol C$_2$Cl$_2$F$_3$I This invention is useful in the production of α,β,β-trifluoroethenyl aromatic compounds including those that are used to fabricate ion exchange membranes or solid polymer electrolytes for use in electrochemical applications such as fuel cells.

Objects and advantages of this invention are further illustrated by the following examples, but the particular materials and amounts thereof recited in these examples, as well as other conditions and details, should not be construed to unduly limit this invention.

EXAMPLES

Unless otherwise noted, all materials were obtained or were available from Aldrich Chemical Co., Milwaukee, Wis.

Ex. 1

A mixture of 139.4 g dichlorotrifluoroiodoethane, C$_2$Cl$_2$F$_3$I, and 58.6 g benzene was sealed in a 220 mL stainless steel autoclave equipped with a nickel rupture disk and a jacket heater. The dichlorotrifluoroiodoethane, C$_2$Cl$_2$F$_3$I, comprised a mixture of 62% CF$_2$ClCFClI and 38% CF$_2$ICFCl$_2$, prepared as described in Example 6 of U.S. Pat. No. 3,002,030, (the teachings of which are incorporated herein by reference) with the exception that the gasseous C$_2$FCl$_3$ reactant was passed into a closed, stirred Hastelloy reaction vessel containing the ICl. The mixture was rocked and heated at 200° C. for 17.5 hours, and the resulting liquid Ex. 2

The reaction was carried out as in Example 1, with the results from the lower temperature and longer reaction time noted in Table 1. The phenyl dichlorotrifluoroethane isomer mixture was isolated by fractional distillation and had the purity and physical constants listed in Table 2. Table 3 reports NMR $^{19}$F shielding values and Gas Chromatographic Retention Indices found for the isomers in this product.

TABLE 2

Purities and Physical Constants of Products

| Ex. # | C$_2$Cl$_2$F$_3$Ar Ar = | GC Purity, wt. % | ClCF$_2$CFClAr isomer % | B.P., °C. (pressure, Torr) | α$^{25}_4$ | n$^{26}_D$ |
|---|---|---|---|---|---|---|
| 2 | —C$_6$H$_5$ | 97.8 | 90.5 | 184–185 (737) | 1.4019 | 1.4714 |
| 3 | —C$_6$H$_4$SO$_2$F | 95.7 | 78 | 140 (25) | 1.5858 | 1.4763 |
| 5 | —C$_6$H$_4$CF$_3$ | 96.8 | 69 | 184–186 (738) | 1.5139 | 1.4282 |
| 7 | —C$_6$H$_3$(CF$_3$)$_2$ (1,3-) | 96.4+ | 81 | 176–178 (740) | 1.6132 | 1.3997 |

TABLE 3

NMR $^{19}$F Shielding Values and Gas Chromatographic Retention Indices[a] of Products

| Ex. # | ClCF$_2$CFClAr Ar = | Cl$_2$CFCF$_2$Ar Ar = | F on α-carbon | F on β-carbon | J$_{AB}$, Hz | CF$_3$ or SO$_2$F | Retention Index[g] | Relative peak area |
|---|---|---|---|---|---|---|---|---|
| 2 | —C$_6$H$_5$ | | −120.34 t[c] | −64.91 d[c] AB[c] −66.63 d | 169 | — | 10.75 | 100 |
| 2 | | —C$_6$H$_5$ | −105.89 d | −72.63 t | | | 10.91 | 10 |
| 3 | —C$_6$H$_4$SO$_2$F (m) | | −121.33 t AB −67.27 d | −66.45 d | 171 | +65.89 | 13.65 | 100 |
| 3 | —C$_6$H$_4$SO$_2$F (non-m) | | −106.53 d | −73.54 t | | +65.87 | 13.81 | 14 |
| 3 | | —C$_6$H$_4$SO$_2$F (m) | −121.49 t | −66.16 d AB −67.06 d | 172 | −65.5 | 13.86 | 9 |
| 3 | | —C$_6$H$_4$SO$_2$F (non-m) | −106.72 d | −73.30 t | | +65.5 | 14.00 | 5 |
| 5 | —C$_6$H$_4$CF$_3$ (m) | | −121.36 t | −66.74 d AB −67.20 d | 171 | −63.34 | 10.24 | 100 |
| 5 | —C$_6$H$_4$CF$_3$ (non-m) | | −106.64 d | −73.34 t | | −63.38 | 10.39[e] | 45[f] |
| 5 | | —C$_6$H$_4$CF$_3$ (m) | −121.43 t | −66.33 d AB −67.10 d | 171 | −63.61 | (10.39)[e] | (45)[f] |
| 5 | | —C$_6$H$_4$CF$_3$ (non-m) | −106.74 d | −73.23 t | | −63.66 | 10.52 | 12 |
| 7 | —C$_6$H$_3$(CF$_3$)$_2$ (1,3,5) | | −121.02 t | −66.35 d AB | 173 | −63.66 | 8.95 | 100 |
| 8 | —C$_6$H$_3$F$_3$ | | — | — | — | — | 10.12 | 100 |
| 8 | | —C$_6$H$_3$F$_3$ | — | — | — | — | 10.26 | 100 |
| 9 | —C$_6$H$_3$F$_3$ | | — | — | — | — | 10.12 | 100 |
| 9 | | —C$_6$H$_3$F$_3$ | — | — | — | — | 10.26 | 75 |

[a]"Programmed Temperature Gas Chromatography", W. E. Harris and H. W. Habgood, Ch. 6, pp. 141–168, John Wiley & Sons, Inc., New York, NY (1966)
[b]G. Filipovich and G. Tiers, J. Phys. Chem., 63 761 (1959)
[c]F-F couplings: d = doublet, t = triplet; AB = asymmetric geminal F$_A$–F$_B$ coupling; J$_{AB}$~170 Hz
[d]Temperature program: 20° C./min from starting temp 40° C.; 5% phenylsilicone capillary column.
[e]Overlapping peaks
[f]Combined peak area
[g]Retention indices are retention times relative to those of the n-alkanes expressed as integral numbers equal to their respective carbon numbers.

Ex. 3

A mixture of 139.4 g C$_2$Cl$_2$F$_3$I (described in Example 1) and 56.1 g benzenesulfonyl fluoride (C$_6$H$_5$—SO$_2$F) was sealed in a stainless steel autoclave equipped with a nickel rupture disk and a jacket heater. The mixture was rocked and heated at 230° C. for 21 hours, and the resulting liquid product was decanted from iodine crystals, a dichloromethane wash of which was combined with the decantate and, as shown in Table 1, determined to contain about 35 g of an isomeric mixture of 20% by weight 3-(2,2-dichloro-1,1,2-trifluoroethyl)benzenesulfonyl fluoride and 80% by weight 3-(1,2-dichloro-1,2,2-trifluoroethyl)benzenesulfonyl fluoride, as determined by NMR spectroscopy, gas chromatography and vacuum fractional distillation. Table 2 reports purities and physical constants found for the resulting products. Table 3 reports NMR $^{19}$F shielding values and Gas Chromatographic Retention Indices found for the resulting product.

Ex. 4

The reaction was carried out as in Example 3, with the results from the lower temperature and longer reaction time noted in Table 1.

Ex. 5

The desired trifluoromethyl compound was prepared as described in Examples 1 and 2 by reaction of 139.4 g C$_2$Cl$_2$F$_3$I (described in Example 1) and 73.1 g trifluoromethylbenzene at 230° C. Analysis of the decanted reaction product, combined with the dichloromethane wash of the iodine crystals, showed it to contain a mixture of isomers, as detailed in Table 1, of which 70% was (1,2-dichloro-1,2,2-trifluoroethyl)trifluoromethylbenzene. The (dichlorotrifluoroethyl)trifluoromethylbenzene isomer mixture was isolated by fractional distillation. Table 2 reports the purity and physical constants found for this product. Table 3 reports NMR $^{19}$F shielding values and Gas Chromatographic Retention Indices found for the isomers in this product.

Ex. 6

The reaction was carried out as in Example 5, with the results from the higher temperature and shorter reaction time noted in Table 1.

Ex. 7

A mixture of 111.5 g C$_2$Cl$_2$F$_3$I (described in Example 1), 11.5 g I$_2$ and 64.2 g 1,3-bis(trifluoromethyl)benzene was heated at 270° C. for 50 hours. Analysis of the reaction product, as detailed in Table 1, showed it to contain about 29 g of a mixture of 5-(1,2-dichloro-1,2,2-trifluoroethyl)-1,3-bis(trifluoromethyl)benzene and 5-(2,2-dichloro-1,1,2- trifluoroethyl)-1,3-bis(trifluoromethyl)benzene in a 78/22 molar ratio. The (dichlorotrifluoroethyl)bis(trifluoromethyl) benzene isomer mixture was isolated by fractional distillation. Table 2 reports the purity and physical constants found for this product. Table 3 reports NMR $^{19}$F shielding values and Gas Chromatographic Retention Indices found for the isomers in this product.

Ex. 8

A mixture of 23.2 g 1,2,4-trifluorobenzene and 195.2 g $C_2Cl_2F_3I$ (described in Example 1) was heated at 230° C. for 20 hours. Table 3 reports Gas Chromatographic Retention Indices found for the isomers of (dichlorotrifluoroethyl)-1, 2,4-trifluorobenzene in this product.

Ex. 9

A mixture of 23.2 g 1,2,4-trifluorobenzene and 195.2 g $C_2Cl_2F_3I$ (described in Example 1) was heated at 280° C. for 16 hours. Table 3 reports Gas Chromatographic Retention Indices found for the isomers of (dichlorotrifluoroethyl)-1, 2,4-trifluorobenzene in this product. In addition to the peaks noted in Table 3, a peak of relative area 18 was seen at retention index 12.68.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3, wherein said reaction is carried out in the presence of added $I_2$.

2. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3, additionally comprising a second step of removing X, X from $(CFX_2CFX)_n$—Ar by dechlorohologenation to form $(CFX=CF)_n$—Ar.

3. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3, additionally comprising a second step of removing X, X from $(CFX_2CFX)_n$—Ar to form $(CFX=CF)_n$—Ar, wherein said step of removing X, X is performed by contacting $(CFX_2CFX)_n$—Ar with zinc metal.

4. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3; additionally comprising a step of sulfonating $(CFX_2CFX)_n$—Ar by reaction with sulfuric acid to form $(CFX_2CFX)_n$—Ar—$(SO_3H)$.

5. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar; additionally comprising a step of sulfonating $(CFX_2CFX)_n$—Ar to form $(CFX_2CFX)_n$—Ar—$(SO_3H)$; wherein Ar is benzene and n=1.

6. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar, wherein n is 1, 2 or 3; additionally comprising a step of reacting $(CFX_2CFX)_n$—Ar with fluorosulfonic acid to form a sulfonyl fluoride of the formula $(CFX_2CFX)_n$—Ar—$(SO_2F)_m$ wherein m is 1 or 2.

7. A process comprising a first step of reacting a first reactant $CFX_2CFXI$, wherein each X is independently F or Cl, provided that at least one X is Cl and at least one X is F, with an aromatic compound Ar to form $(CFX_2CFX)_n$—Ar, additionally comprising a step of reacting $(CFX_2CFX)_n$—Ar to form a sulfonyl fluoride of the formula $(CFX_2CFX)_n$—Ar—$(SO_2F)_m$; wherein Ar is benzene, n=1 and m=1.

8. The process of claim 2 additionally comprising a step of polymerizing or copolymerizing $(CF_2=CF)_n$—Ar to form a polymer or copolymer that includes units having the formula —$(CF_2$—$CF(Ar))$—.

9. The process of claim 5 additionally comprising a step of polymerizing or copolymerizing $(CF_2=CF)$—$C_6H_4$—$(SO_3H)$ to form a polymer or copolymer that includes units having the formula —$(CF_2$—$CF(C_6H_4$—$SO_3H))$—.

10. The process of claim 7 additionally comprising a step of polymerizing $(CF_2=CF)$—$C_6H_4$—$(SO_2F)$ to form a polymer or copolymer that includes units having the formula —$(CF_2$—$CF(C_6H_4$—$SO_2F))$—.

11. The process of claim 8 additionally comprising a step of sulfonating said polymer or copolymer by reaction with sulfuric acid.

12. The compound $(CFCl_2CF_2)_n$—Ar, wherein n is 2 or 3 and Ar is unsubstituted benzene.

13. The compound $(CFCl_2CF_2)_n$—Ar wherein n is 1, 2 or 3 and wherein Ar is selected from the group consisting of disubstituted benzene and polysubstituted benzene bearing 3–5 substituents.

14. The compound of claim 13 wherein n is 1.

15. The compound $(CFX_2CFX)_n$—Ar, wherein each X is independently F or Cl, provided that at least one X of each $(CFX_2CFX)$ group is Cl and at least one X of each $(CFX_2CFX)$ group is F, wherein Ar is selected from the group consisting of monosubstituted benzene, disubstituted benzene and polysubstituted benzene bearing 3–5 substituents and wherein n is 2 or 3.

16. The compound of claim 15 wherein benzene substituents are independently selected from the group consisting of phenyl, fluoro, perfluoroalkyl, fluorocarbonyl, fluorosulfonyl, and difluorophosphonyl.

17. The compound $(CFX_2CFX)$—Ar, wherein each X is independently F or Cl, provided that at least one X is Cl and at least one X is F, wherein Ar is disubstituted benzene, and wherein benzene substituents are independently selected from the group consisting of phenyl, fluoro, perfluoroalkyl, fluorocarbonyl, fluorosulfonyl, and difluorophosphonyl.

18. The compound $(CFX_2CFX)$—Ar, wherein each X is independently F or Cl, provided that at least one X is Cl and at least one X is F, wherein Ar is trisubstituted benzene, and wherein benzene substituents are independently selected from the group consisting of phenyl, fluoro, perfluoroalkyl, fluorocarbonyl, fluorosulfonyl, and difluorophosphonyl.

19. The compound of claim 16 wherein Ar is monosubstituted benzene.

20. The compound of claim 16 wherein Ar is disubstituted benzene.

21. The compound $CF_3CFCl$—Ar, wherein At is selected from the group consisting of monosubstituted benzene and disubstituted benzene.

* * * * *

UNITED STATES PATENT AND TRADEMARK OFFICE
CERTIFICATE OF CORRECTION

PATENT NO. : 6,350,925 B1  Page 1 of 1
DATED : February 26, 2002
INVENTOR(S) : Tiers, George V. D.

It is certified that error appears in the above-identified patent and that said Letters Patent is hereby corrected as shown below:

Title page,
Item [56], U.S. PATENT DOCUMENTS, delete the issue date of "6/1969" for 3,449,449 and insert -- 6/1995 --.

Column 2,
Line 10, delete "β".

Columns 7 & 8,
Table 3, under subheading "F on α-carbon" delete "    AB
                                                -67.27d".
Table 3, under subheading "F on β-carbon" "-66.45 d" should read -- -66.45 d
                                                                        AB
                                                                    -67.27 d --.
Table 3, under subheading "F on β-carbon" "-66.35 d    should read -- -66.35 d
                                                AB"                        AB
                                                                    -67.22 d --.
Column 10,
Line 62, after "wherein", delete "At" and insert in place thereof -- Ar --.

Signed and Sealed this

Seventeenth Day of June, 2003

JAMES E. ROGAN
*Director of the United States Patent and Trademark Office*